United States Patent
Swanson et al.

(10) Patent No.: US 9,379,507 B2
(45) Date of Patent: Jun. 28, 2016

(54) FEEDTHROUGH SYSTEM FOR IMPLANTABLE DEVICE COMPONENTS

(71) Applicant: Cardiac Pacemakers, Inc., St. Paul, MN (US)

(72) Inventors: Lawrence D. Swanson, White Bear Lake, MN (US); John M. Edgell, Plymouth, MN (US); John E. Hansen, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 261 days.

(21) Appl. No.: 14/084,227

(22) Filed: Nov. 19, 2013

(65) Prior Publication Data

US 2014/0075752 A1   Mar. 20, 2014

Related U.S. Application Data

(62) Division of application No. 13/028,532, filed on Feb. 16, 2011, now Pat. No. 8,612,003.

(60) Provisional application No. 61/315,455, filed on Mar. 19, 2010.

(51) Int. Cl.
*A61N 1/36* (2006.01)
*H01R 43/16* (2006.01)
(Continued)

(52) U.S. Cl.
CPC ............. *H01R 43/16* (2013.01); *A61N 1/375* (2013.01); *A61N 1/3758* (2013.01); *A61N 1/3968* (2013.01); *Y10T 29/49002* (2015.01); *Y10T 29/49208* (2015.01)

(58) Field of Classification Search
CPC ... A61N 1/375; A61N 1/3758; A61N 1/3968; H01R 43/16; Y01T 29/49208
USPC ...................................................... 607/36–37
See application file for complete search history.

(56) References Cited

U.S. PATENT DOCUMENTS

| 4,310,001 A | 1/1982 | Comben |
| 5,103,818 A | 4/1992 | Maston et al. |

(Continued)

FOREIGN PATENT DOCUMENTS

| WO | WO-2006089682 A2 | 4/2006 |
| WO | WO-2011115719 A1 | 9/2011 |

OTHER PUBLICATIONS

"U.S. Appl. No. 13/028,532, Response filed Apr. 17, 2013 to Non Final Office Action mailed Jan. 17, 2013", 7 pgs.

(Continued)

*Primary Examiner* — Amanda Patton
(74) *Attorney, Agent, or Firm* — Schwegman Lundberg & Woessner, P.A.

(57) ABSTRACT

The present subject matter provides feedthrough or interconnect systems for components of an implantable medical device and methods for their manufacture. A feedthrough system includes a wire or nailhead having a protruded tip. The wire or nailhead extends from an aperture in an encasement of a first component and is connected to a terminal conductor adapted to electrically connect to circuitry within the encasement. A ribbon wire has a distal end adapted to electrically connect to a second component and a proximal end having a pattern adapted to fit to the protruded tip of the wire or nailhead to provide for subsequent attachment of the ribbon wire to the nailhead.

20 Claims, 6 Drawing Sheets

(51) Int. Cl.
  *A61N 1/375* (2006.01)
  *A61N 1/39* (2006.01)

(56) References Cited

U.S. PATENT DOCUMENTS

| | | |
|---|---|---|
| 5,314,451 A | 5/1994 | Mulier |
| 5,735,884 A | 4/1998 | Thompson et al. |
| 5,782,891 A * | 7/1998 | Hassler ............... A61N 1/3754 607/36 |
| 6,006,135 A | 12/1999 | Kast et al. |
| 6,026,325 A | 2/2000 | Weinberg et al. |
| 6,052,623 A | 4/2000 | Fenner et al. |
| 6,052,625 A | 4/2000 | Marshall |
| 6,191,931 B1 | 2/2001 | Paspa et al. |
| 6,256,542 B1 | 7/2001 | Marshall et al. |
| 6,402,793 B1 | 6/2002 | Miltich et al. |
| 6,899,976 B2 | 5/2005 | Larson et al. |
| 7,630,768 B1 | 12/2009 | Coffed et al. |
| 2006/0089682 A1 | 4/2006 | Kronich et al. |
| 2009/0204172 A1* | 8/2009 | Wegrzyn, III ........ A61N 1/3754 607/36 |
| 2011/0230923 A1 | 9/2011 | Swanson et al. |

OTHER PUBLICATIONS

"U.S. Appl. No. 13/028,532, Non Final Office Action mailed Jan. 17, 2013", 8 pgs.

"U.S. Appl. No. 13/028,532, Notice of Allowance mailed Aug. 19, 2013", 8 pgs.

"U.S. Appl. No. 13/028,532, Response filed Jan. 3, 2013 to Restriction Requirement mailed Dec. 3, 2012", 6 pgs.

"U.S. Appl. No. 13/028,532, Restriction Requirement mailed Dec. 3, 2012", 5 pgs.

"International Application Serial No. PCT/US2011/025009, International Preliminary Report on Patentability mailed Oct. 4, 2012", 7 pgs.

"International Application Serial No. PCT/US2011/025009, International Search Report mailed May 3, 2011", 4 pgs.

"International Application Serial No. PCT/US2011/025009, Written Opinion mailed May 3, 2011", 6 pgs.

\* cited by examiner

FEEDTHROUGH SYSTEM FOR IMPLANTABLE DEVICE COMPONENTS

CLAIM OF PRIORITY

This application is a division of U.S. application Ser. No. 13/028,532, filed Feb. 16, 2011, now issued as U.S. Pat. No. 8,612,003, which claims the benefit of priority under 35 U.S.C. §119(e) of U.S. Provisional Patent Application Ser. No. 61/315,455, filed on Mar. 19, 2010, each of which is herein incorporated by reference in its entirety.

TECHNICAL FIELD

This application relates generally to implantable medical devices, and more particularly, to feedthrough interconnects for components of implantable medical devices.

BACKGROUND

Sealed encasement (i.e., a container) can provide electrical access to or from electrical components enclosed within. One application involves body implantable medical devices (referred to as "IMDs"), such as pulse generators or cardiac function management devices, for the treatment of bradycardia, tachyarrhythmia, or muscle or nerve stimulation. An example involves providing electrical access to and from a power source (e.g., a battery) of an IMD.

Electrical feedthrough assemblies provide a conductive path extending between the interior of the hermetically sealed encasement and a location outside the encasement. Typically, the conductive path comprises a conductive pin or other type of terminal that is electrically insulated from the encasement. In addition, feedthrough assemblies may include a ferrule and an insulative material for positioning and insulating the pin within the ferrule. In the battery power source example, a conductive connection member is often directly coupled to an internal portion (i.e., a portion located within the battery encasement) of the conductive pin on a first end and coupled to an anode or cathode of the battery on a second end.

Interconnections to components are typically made with feedthrough wires that are routed in the header to connector blocks and then spot-welded. This requires a multi-step operation involving wire bending, multiple applications of medical adhesive, and significant manual interaction with the components. Bending wires and installing tubing can increase manufacturing time and cost, and expose the hardware to physical damage.

SUMMARY

Various embodiments disclosed herein provide feedthrough assemblies that comprise, among other things, highly reliable components and secure interconnections. The present subject matter provides feedthrough or interconnect systems for components of an implantable medical device and methods for their manufacture. A feedthrough system includes a wire or nailhead having a protruded tip. The wire or nailhead extends from an aperture in an encasement of a first component and is connected to a terminal conductor adapted to electrically connect to circuitry within the encasement. A ribbon wire has a distal end adapted to electrically connect to a second component and a proximal end having a pattern adapted to snap-fit to the wire or the protruded tip of the nailhead to provide for subsequent attachment of the ribbon wire to the nailhead. The subsequent attachment can include an adhesive or welding, such as laser welding.

In various embodiments, an implantable medical device is provided. The device includes a first component with an encasement, the encasement having a feedthrough including a nailhead having a protruded tip. The nailhead extends from an aperture in the encasement and connects to a terminal conductor adapted to electrically connect to circuitry within the encasement. The device also includes a ribbon wire with a proximal end having a pattern adapted to snap-fit to the protruded tip of the nailhead to provide for subsequent laser welding of the ribbon wire to the nailhead. The device further includes a second component electrically connected to a distal end of the ribbon wire.

In one embodiment, a method for manufacturing an implantable medical device is provided. The method includes forming a nailhead having a protruded tip. The nailhead extends from an aperture in an encasement of a first component and is connected to a terminal conductor adapted to electrically connect to circuitry within the encasement. A ribbon wire is formed having a distal end adapted to electrically connect to a second component and a proximal end having a pattern. The proximal end of the ribbon wire is connected to the protruded tip of the nailhead, including snap-fitting the pattern of the ribbon wire to the protruded tip of the nailhead.

In an embodiment, a method for electrically connecting components of an implantable medical device is provided. The implantable medical device has a first and second component, the first component including a nailhead having a protruded tip extending from an aperture in an encasement of the first component. The method includes snap-fitting a pattern on a proximal end of a ribbon wire to the protruded tip of the nailhead, the ribbon wire having a distal end adapted to electrically connect to the second component. The method also includes welding the ribbon wire to the nailhead.

This summary is an overview of some of the teachings of the present application and is not intended to be an exclusive or exhaustive treatment of the present subject matter. Further details about the present subject matter are found in the detailed description. The scope of the present invention is defined by the appended claims and their equivalents.

DETAILED DESCRIPTION

Figure 1A:
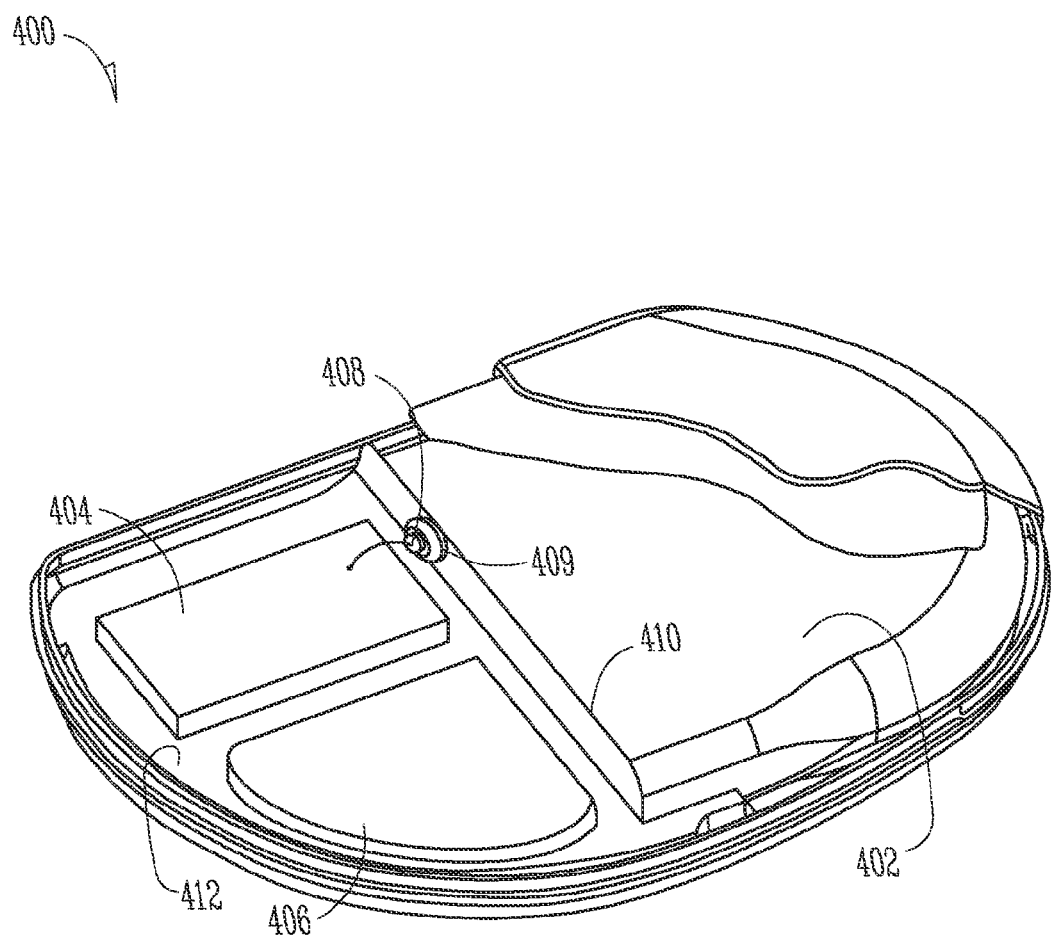
FIG. 1A illustrates an example of an implantable medical device.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Patients prone to irregular heart rhythms sometimes have miniature heart devices, such as defibrillators and cardioverters, implanted in their bodies. These devices detect onset of abnormal heart rhythms and apply corrective electrical therapy to the heart. The defibrillator or cardioverter includes a set of electrical leads, which extend from a device housing into the heart. Components can have their own housings or encasements, and require apertures in the encasement with a feedthrough conductor or interconnect protruding from the aperture to connect to a main circuit board of the device.

The present subject matter provides feedthrough or interconnect systems for components of an implantable medical device and methods for their manufacture. A feedthrough system embodiment includes a wire or a nailhead having a protruded Tip. The wire or nailhead extends from an aperture in an encasement of a first component and is connected to a terminal conductor adapted to electrically connect to circuitry within the encasement. A ribbon wire has a distal end adapted to electrically connect to a second component and a proximal end having a pattern adapted to fit to the wire or the protruded tip of the nailhead to provide for subsequent attachment of the ribbon wire to the nailhead. Fitting refers to placing the pattern over the protruded tip for a fixturing/locating function, such as a press form feature, in various embodiments. According to various embodiments, fitting includes snap-fitting of the pattern onto the wire or the protruded tip.

According to various embodiments, the feedthrough system is adapted to connect a battery cell or a capacitor to the main circuit board. In various embodiments, an implantable medical device is provided. The device includes a first component with an encasement, the encasement having a feedthrough including a nailhead having a protruded tip. The nailhead extends from an aperture in the encasement and connects to a terminal conductor adapted to electrically connect to circuitry within the encasement. The device also includes a ribbon wire with a proximal end having a pattern adapted to snap-fit to the protruded tip of the nailhead to provide for subsequent laser welding of the ribbon wire to the nailhead. The device further includes a second component electrically connected to a distal end of the ribbon wire.

A nailhead includes a relatively flat portion adapted to snap-fit with a pattern of a portion of ribbon, according to various embodiments. In various embodiments, a wire protruding from an encasement is used instead of a nailhead. The ribbon has a pattern including an aperture sized to be pressed over a wire tip or a nailhead and snap onto the wire tip or the nailhead, in various embodiments. According to various embodiments, a tang refers to a pattern projected and etched onto the ribbon wire such that material has been removed forming an opening to allow the ribbon to be formable for placement over the wire tip or nailhead. A tang pattern refers to the pattern of the opening on the end of the ribbon, adapted for bending of the flexible ribbon to place the opening over the wire tip or the nailhead, and flexing back into place to fit to the wire tip or nailhead. A multiple tang pattern includes an aperture with multiple corners, in various embodiments.

Interconnections from components such as battery cells or capacitors to the main circuit board (or hybrid board) of the implantable medical device can be difficult to make considering different planes of attachment. The typical component connector comes out of the component encasement on a radial axis of the encasement, which makes the connector parallel to the board. Thus, the connector or the board would be substantially bent to make the connection.

Interconnections to components are typically made with feed through wires that are routed in the header to connector blocks and then spot-welded. This requires a multi-step operation involving wire bending, multiple applications of medical adhesive, and significant manual interaction with the components. In addition, components and their interconnections can take up significant volume in the device. Bending wires and installing tubing can increase manufacturing time and cost, and expose the hardware to physical damage. FIG. 1A illustrates an example of an encasement for a component of an implantable medical device.

In FIG. 1A, an example of an IMD 400 is illustrated. In this example, IMD 400 includes a power source section 402, an electronics section 404, a capacitor section 406, and one or more feedthrough assemblies 408. The "IMD" will typically include, among other things, cardiac function management (referred to as "CFM") systems such as pacemakers, cardioverters/defibrillators, paces/defibrillators, biventricular or other multi-site resynchronization or coordination devices such as cardiac resynchronization therapy (referred to as "CRT") devices, or drug delivery systems.

Power source section 402 may include, but is not limited to, an electrochemical cell, an electrolytic or other capacitor, or a battery. In one example, power source section 402 comprises a battery having an anode or a cathode terminal and is enclosed by an encasement 410, such as a can or other container. In the example, encasement 410 includes at least one encasement aperture 409 into which the one or more feedthrough assemblies 408 are mounted. As discussed, feedthrough assembly 408 penetrates the otherwise sealed encasement 410, such as to provide electrical access to or from one or more electrical components (e.g., an anode or a cathode terminal) enclosed therewithin.

FIG. 1A illustrates one example of various sections and assemblies of an IMD 400. Power source section 402, electronics section 404, capacitor section 406, circuit board 412, and the one or more feedthrough assemblies 408 are illustrated separately for conceptual clarity; however, such sections and assemblies may be further separated or need not be separately embodied.

Figure 1B:
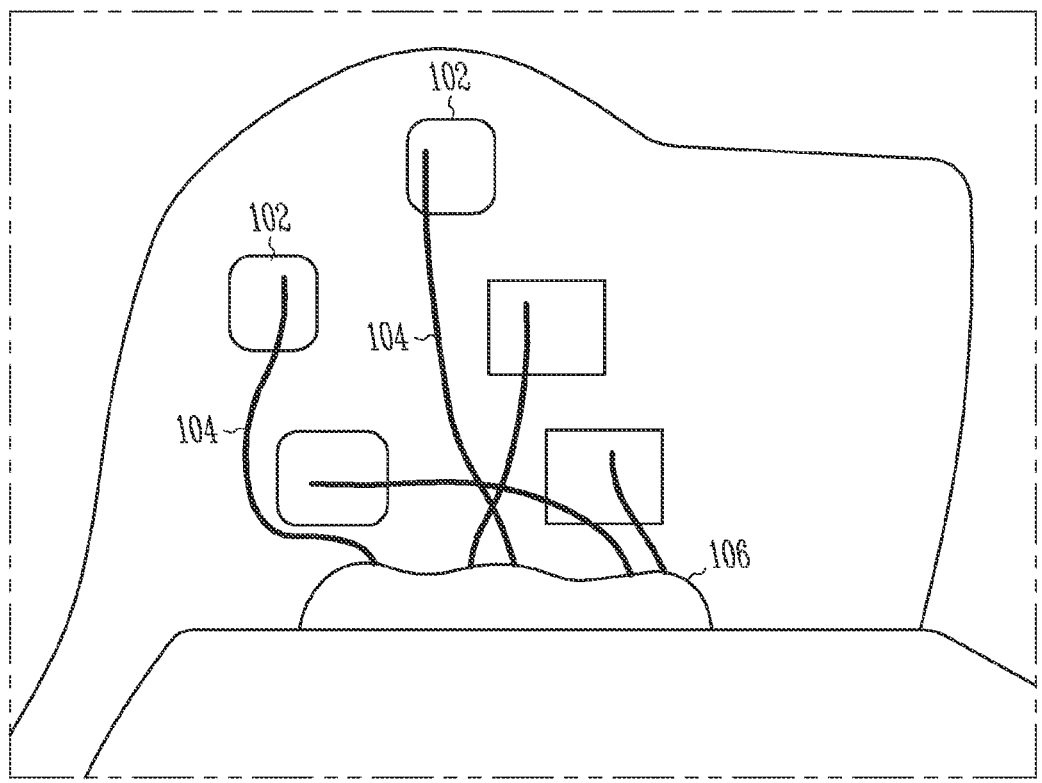
FIG. 1B illustrates an example of an implantable medical device interconnect.
Figure 1C:
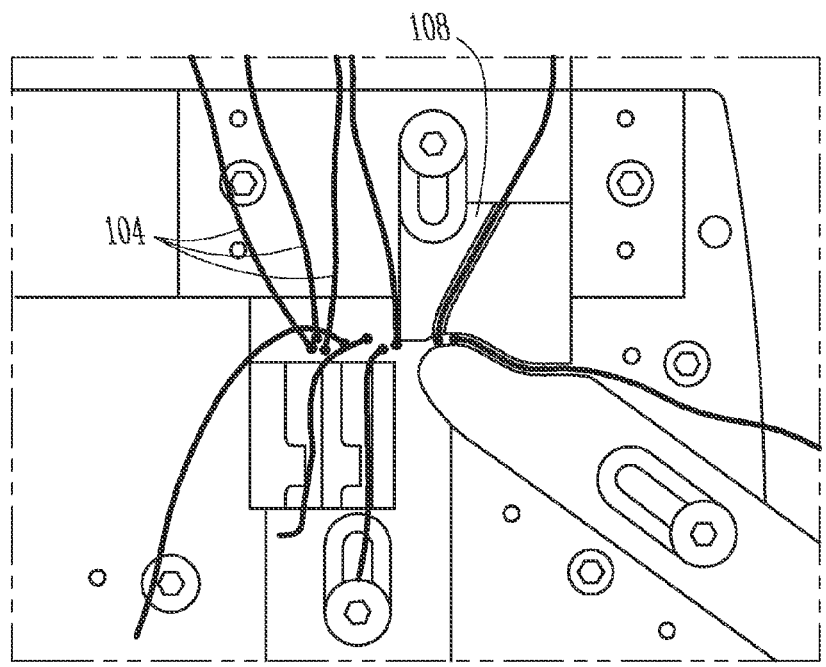
FIG. 1C illustrates an example of bending wires for connecting a component of an implantable medical device.
Figure 1D:
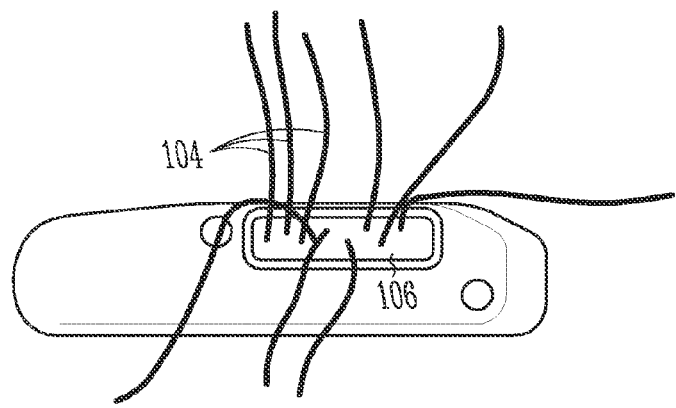
FIG. 1D illustrates an example of bent wires connecting a component of an implantable medical device.

FIG. 1B illustrates an example of an implantable medical device interconnect. Electrical connections are made from a feedthrough 106 in a first component to connector blocks 102, or headers, of various other components or circuits. Electrical wires 104 are routed from the feedthrough 106 to the connector blocks 102 and subsequently spot welded to the connector blocks. FIG. 1C illustrates an example of bending wires 104 for connecting a component of an implantable medical device. A manual wire bending fixture 108 is used to secure the component for bending wires that connect or are protruding from the feedthrough 106. FIG. 1D illustrates an example of bent wires 104 after using the fixture 108, and before attaching the wires to a connector block. The interconnect conductors protrude through the apertures to mate with the main circuit board. However, the location of the feedthrough apertures requires bending of the wires and/or circuit board to properly line up with the conductors. The interconnect space can take up significant volume in the IMD. Bending wires and boards is a burden for manufacturing and may cause damage to the device or component connections.

Figure 2A:
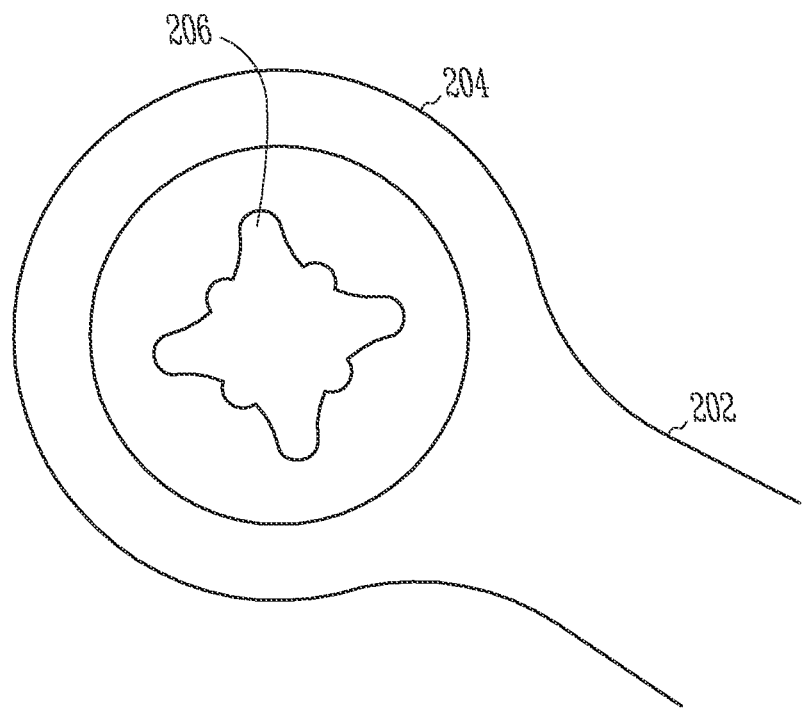
FIG. 2A illustrates a portion of a ribbon wire for a feedthrough interconnect, according to an embodiment of the present subject matter.

FIG. 2A illustrates a portion of a ribbon wire for a feedthrough interconnect, according to an embodiment of the present subject matter. The ribbon wire 202 has a proximal end 204 with a pattern 206 etched therein. The depicted pattern 206 is a four tang pattern, but other patterns can be used without departing from the scope of this disclosure. The pattern 206 is also a press form feature, in an embodiment. The pattern is selected to provide a snap-fit mating to a protrusion (a protruding wire tip or a nailhead) from a feedthrough, in various embodiments.

Figure 2B:
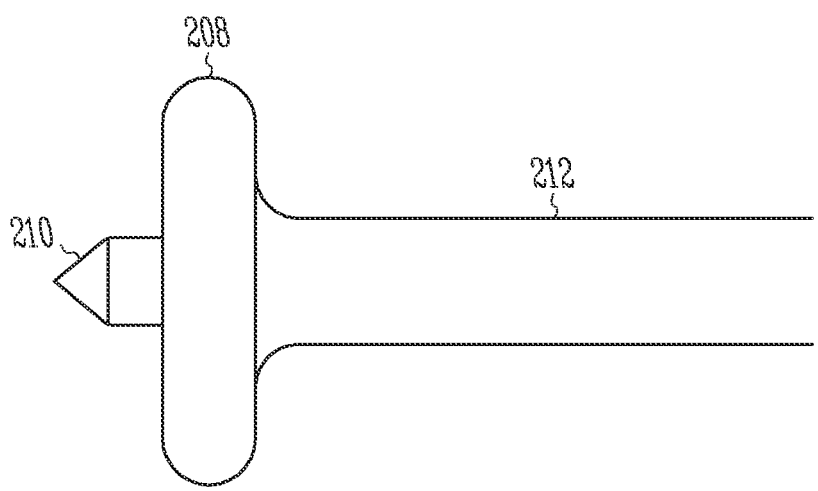
FIG. 2B illustrates a nailhead for a feedthrough interconnect, according to an embodiment of the present subject matter.

FIG. 2B illustrates a nailhead for a feedthrough interconnect, according to an embodiment of the present subject matter. The nailhead 208 has a protruded tip 210 for mating with a pattern on a ribbon wire. According to various embodiments, the nailhead 208 is connected to a wire or terminal conductor 212 to electrically connect to electronics within a component. Nailheads are made using a standard heading technology with small changes to the tooling to allow for a protrusion feature, in various embodiments. Various embodiments of the present subject matter use wire tips protruding from a feedthrough in addition to, or instead of the depicted nailheads. The ribbon is pressed onto the wire tip and subsequently attached using welding or an adhesive. A nailhead has the advantage of protecting structure or wiring under the head, in various embodiments.

Figure 2C:
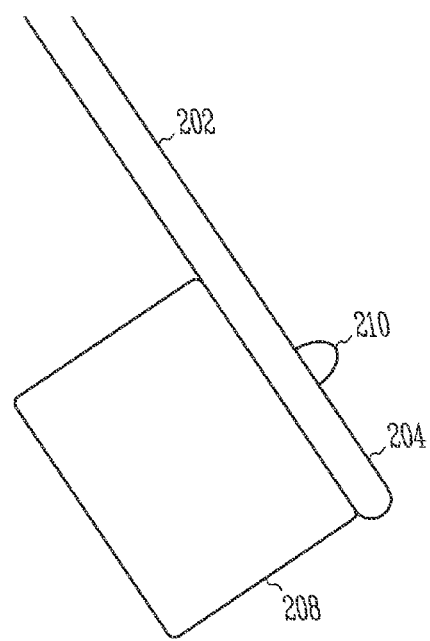
FIG. 2C illustrates a feedthrough interconnection for implantable components, the feedthrough interconnection including a ribbon wire and a nailhead, according to an embodiment of the present subject matter.

FIG. 2C illustrates a feedthrough interconnection for implantable components, the feedthrough interconnection including a ribbon wire 202 and a nailhead 208, according to an embodiment of the present subject matter. The proximal end 204 of the ribbon wire 202 is shown connected to the protrusion 210 of the nailhead 208. The proximal end 204 is snap-fit to the protrusion 210, in various embodiments. The resulting robust temporary connection protects surrounding components and decreases the size of the implantable device. The ribbon wire 202 is manufactured using an etching process, in various embodiments. The etching process includes a chemical etching process, in an embodiment. In another embodiment, the etching process includes a laser etching process. In an embodiment, the ribbon wire has features etched into the tip that allow for a temporary snap fit to hold the components together such that subsequent laser welding can permanently fix the components. The features in the ribbon wire allow the parts to be preassembled outside the laser weld system, in various embodiments.

Figure 2D:
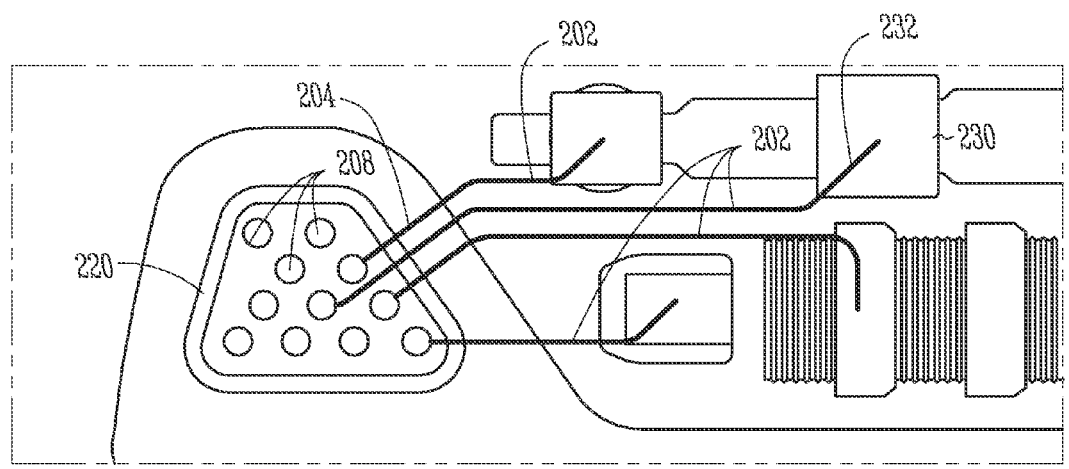
FIG. 2D illustrates a feedthrough system for implantable components, according to an embodiment of the present subject matter.

FIG. 2D illustrates a feedthrough system for implantable components, according to an embodiment of the present subject matter. The feedthrough 220 has a number of nailheads 208, in various embodiments. Ribbon wires 202 have proximal ends 204 connected to nailheads 208, and distal ends 232 electrically connected to connector blocks 230 of other components or circuitry.

The present subject matter provides feedthrough systems for components of an implantable medical device and methods for their manufacture. A feedthrough system embodiment includes a nailhead having a protruded tip. The nailhead extends from an aperture in an encasement of a first component and is connected to a terminal conductor adapted to electrically connect to circuitry within the encasement. A ribbon wire has a distal end adapted to electrically connect to a second component and a proximal end having a pattern adapted to snap-fit to the protruded tip of the nailhead to provide for subsequent laser welding of the ribbon wire to the nailhead. According to various embodiments, the feedthrough system is adapted to connect a battery cell or a capacitor to the main circuit board. According to various embodiments, the pattern includes a press form feature. The pattern includes a tang pattern, such as a four-tang pattern, in various embodiments. According to various embodiments, the circuitry includes a main circuit board and the second component includes a battery cell or a capacitor. The main circuit board includes a hybrid circuit or flex circuit, in various embodiments. The present subject matter can be used with a variety of implantable medical device, including but not limited to pacemakers, defibrillators and neural stimulators.

Figure 3:
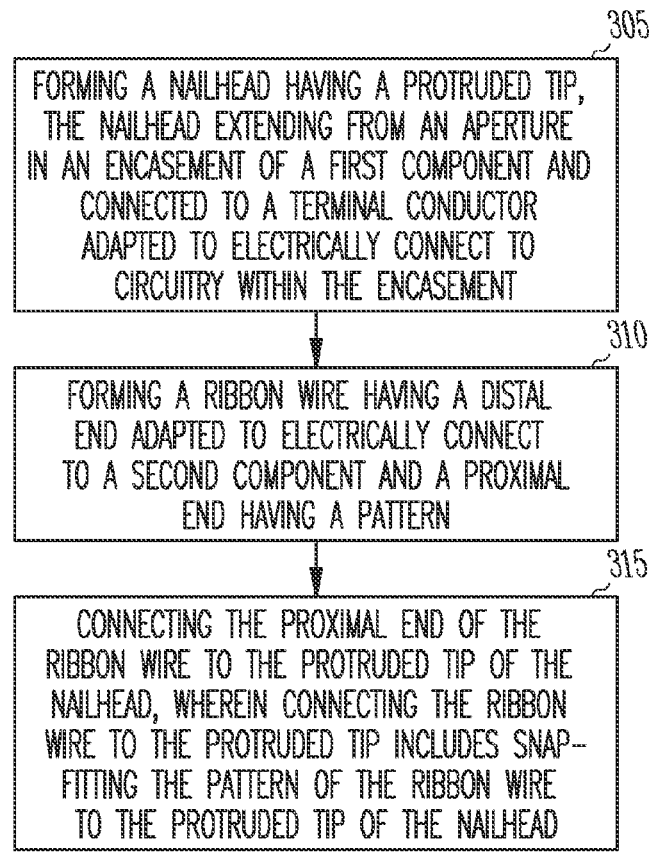
FIG. 3 is a flow chart illustrating an embodiment of a method for manufacturing of an implantable medical device.

FIG. 3 is a flow chart illustrating an embodiment of a method for manufacturing an implantable medical device. The method includes forming a nailhead having a protruded tip, at 305. The nailhead extends from an aperture in an encasement of a first component and is connected to a terminal conductor adapted to electrically connect to circuitry within the encasement. At 310, a ribbon wire is formed having a distal end adapted to electrically connect to a second component and a proximal end having a pattern. At 315, the proximal end of the ribbon wire is connected to the protruded tip of the nailhead, including snap-fitting the pattern of the ribbon wire to the protruded tip of the nailhead.

According to various embodiments, connecting the proximal end of the ribbon wire to the protruded tip of the nailhead further comprises laser welding the ribbon wire to the nailhead. The laser welding is subsequent to snap-fitting, in an embodiment. Forming a nailhead having a protruded tip includes using a tool and die with adjustments to the tool to provide the protruded tip, in various embodiments. According to various embodiments, forming a ribbon wire having a pattern includes etching the pattern into the ribbon wire. The etching process includes a chemical etching process, in an embodiment. In another embodiment, the etching process includes a laser etching process. Various method embodiments further include connecting the terminal conductor from a battery cell or capacitor to a main circuit board. In some embodiments, for example, the battery cell is adapted to power the IMD, and the capacitor is adapted to store charge for delivery of electrical therapy by the IMD, in various embodiments.

In an embodiment, a method for electrically connecting components of an implantable medical device is provided. The implantable medical device has a first and second component, the first component including a nailhead having a protruded tip extending from an aperture in an encasement of the first component. The method includes snap-fitting a pattern on a proximal end of a ribbon wire to the protruded tip of the nailhead, the ribbon wire having a distal end adapted to electrically connect to the second component. The method also includes welding the ribbon wire to the nailhead.

Figure 4:
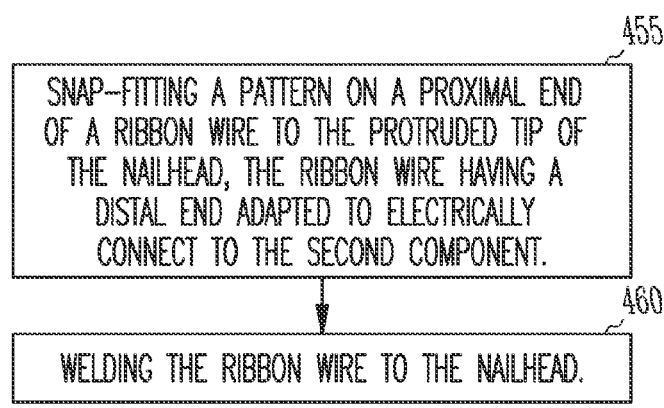
FIG. 4 is a flow chart illustrating an embodiment of a method for electrically connecting components of an implantable medical device.

FIG. 4 is a flow chart illustrating an embodiment of a method for electrically connecting components of an implantable medical device. The implantable medical device has a first and second component, the first component including a nailhead having a protruded tip extending from an aperture in an encasement of the first component. At 405, the method includes snap-fitting a pattern on a proximal end of a ribbon wire to the protruded tip of the nailhead, the ribbon wire having a distal end adapted to electrically connect to the second component. The method also includes welding the ribbon wire to the nailhead, at 410.

According to various embodiments, welding the ribbon wire to the nailhead includes laser welding the ribbon wire to the nailhead. The method further includes connecting the nailhead to a terminal conductor adapted to electrically connect to circuitry within the encasement, according to various embodiments.

The present subject matter provides for simplified connections between sealed components and a main IMD circuit board. Advantages include decreased overall device size, yield enhancements due to ease of assembly, reduced part counts, and elimination of bending that can compromise structural integrity of circuits and conductors. In addition, the present subject matter provides for decreased tubing, wire bending, applications of medical adhesive, and manual interaction with components, resulting in reduced development time and associated benefits. Also, the present subject matter provides for fixtureless assembly with z-axis assembly options, resulting in reduced development time and associated benefits.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for manufacturing an implantable medical device having a first and second component, the method comprising:
    forming a nailhead having a protruded tip, the nailhead extending from an aperture in an encasement of the first component and connected to a terminal conductor adapted to electrically connect to circuitry within the encasement;
    forming a ribbon wire having a distal end adapted to electrically connect to the second component and a proximal end having a pattern including an aperture through the ribbon wire sized to fit over the protruded tip; and
    connecting the proximal end of the ribbon wire to the protruded tip of the nailhead, wherein connecting the proximal end of the ribbon wire to the protruded tip includes snap-fitting the pattern of the ribbon wire to the protruded tip of the nailhead.

2. The method of claim 1, wherein connecting the proximal end of the ribbon wire to the protruded tip of the nailhead further comprises laser welding the ribbon wire to the nailhead.

3. The method of claim 2, wherein laser welding is subsequent to snap-fitting.

4. The method of claim 1, wherein forming a nailhead having a protruded tip includes using a tool and die with adjustments to the tool to provide the protruded tip.

5. The method of claim 1, wherein forming a ribbon wire having a pattern includes etching the pattern into the ribbon wire.

6. The method of claim 1, further comprising:
    connecting the terminal conductor to a battery cell.

7. The method of claim 6, wherein connecting the terminal conductor to a battery cell includes connecting to a battery cell adapted to power the implantable medical device.

8. The method of claim 1, wherein the implantable medical device includes a neural stimulator.

9. The method of claim 1, wherein the implantable medical device includes a pacemaker.

10. The method of claim 1, wherein the implantable medical device includes a defibrillator.

11. A method for electrically connecting components of an implantable medical device having a first and second component, the first component including a nailhead having a protruded tip extending from an aperture in an encasement of the first component, the method comprising:
    snap-fitting a pattern on a proximal end of a ribbon wire to the protruded tip of the nailhead, the pattern including an aperture through the ribbon wire sized to fit over the protruded tip, and the ribbon wire having a distal end adapted to electrically connect to the second component; and
    welding the ribbon wire to the nailhead.

12. The method of claim 11, wherein welding the ribbon wire to the nailhead includes laser welding the ribbon wire to the nailhead.

13. The method of claim 11, further comprising connecting the nailhead to a terminal conductor adapted to electrically connect to circuitry within the encasement.

14. The method of claim 11, wherein snap-fitting the pattern includes snap-fitting a press form feature.

15. The method of claim 11, wherein snap-fitting the pattern includes snap-fitting a tang pattern.

16. The method of claim 11, wherein the first component includes a main circuit board.

17. The method of claim 16, wherein the main circuit board includes a hybrid circuit.

18. The method of claim 16, wherein the main circuit board includes a flex circuit.

19. The method of claim 11, wherein the second component includes a battery.

20. The method of claim 11, wherein the second component includes a capacitor.

* * * * *